United States Patent
Macdonald et al.

(10) Patent No.: US 9,402,962 B2
(45) Date of Patent: Aug. 2, 2016

(54) ASSEMBLY FOR USE IN A DRUG DELIVERY DEVICE

(75) Inventors: Catherine Anne Macdonald, Ashby-de-la-Zouch (GB); Robert Veasey, Leamington Spa (GB); Garen Kouyoumjian, Leamington Spa (GB); Christopher Jones, Tewkesbury (GB); Andrew Mark Lindsay, Hinckley (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1151 days.

(21) Appl. No.: 13/497,375

(22) PCT Filed: Sep. 29, 2010

(86) PCT No.: PCT/EP2010/064409
§ 371 (c)(1),
(2), (4) Date: Jul. 23, 2012

(87) PCT Pub. No.: WO2011/039218
PCT Pub. Date: Apr. 7, 2011

(65) Prior Publication Data
US 2012/0283650 A1 Nov. 8, 2012

(30) Foreign Application Priority Data
Sep. 30, 2009 (EP) ..................................... 09171750

(51) Int. Cl.
*A61M 5/00* (2006.01)
*A61M 5/315* (2006.01)
(Continued)

(52) U.S. Cl.
CPC ......... *A61M 5/31593* (2013.01); *A61M 5/3146* (2013.01); *A61M 5/31555* (2013.01);
(Continued)

(58) Field of Classification Search
CPC ...................... A61M 5/31551; A61M 5/31575; A61M 5/31585; A61M 2005/3152; A61M 5/31541
USPC .................................................. 604/207–211
See application file for complete search history.

(56) References Cited

U.S. PATENT DOCUMENTS 6,193,698 B1    2/2001  Kirchhofer et al.
8,197,450 B2 *  6/2012  Glejbol ............. A61M 5/31551
                                                    604/207

(Continued)

OTHER PUBLICATIONS

European Search Report for European App. No. 09171750, completed Mar. 11, 2010.

(Continued)

*Primary Examiner* — Phillip Gray
(74) *Attorney, Agent, or Firm* — McDonnell Boehnen Hulbert & Berghoff LLP

(57) ABSTRACT

The present invention relates to an assembly for a drug delivery device comprising a proximal end, a distal end and a moveable member, a dose member, a fixed member and coupling means, wherein in a first state, the moveable member is moveable in an axial direction with respect to the fixed member and the dose member and the coupling means retains the dose member to the fixed member, and wherein in a second state of the assembly, the moveable member is permanently connected with the dose member by means of the coupling means and the dose member is released from the fixed member and the assembly is configured to set and dispense a dose of a fluid medicinal product out of an assembled cartridge by movement of the dose member. Furthermore it relates to a method for setting-up a drug delivery device.

23 Claims, 6 Drawing Sheets

(51) Int. Cl.
   *A61M 5/31* (2006.01)
   *A61M 5/24* (2006.01)
(52) U.S. Cl.
   CPC ............. *A61M 5/24* (2013.01); *A61M 5/31501* (2013.01); *A61M 5/31511* (2013.01); *A61M 2005/2407* (2013.01); *A61M 2205/581* (2013.01)

(56) References Cited

U.S. PATENT DOCUMENTS

2005/0222540 A1   10/2005   Kirchhofer et al.
2007/0016142 A1   1/2007   Burren et al.

OTHER PUBLICATIONS

International Search Report for International App. No. PCT/EP2010/064409, completed Nov. 16, 2010.
International Preliminary Report on Patentability for International App. No. PCT/EP2010/062433, issued Feb. 28, 2012.

* cited by examiner

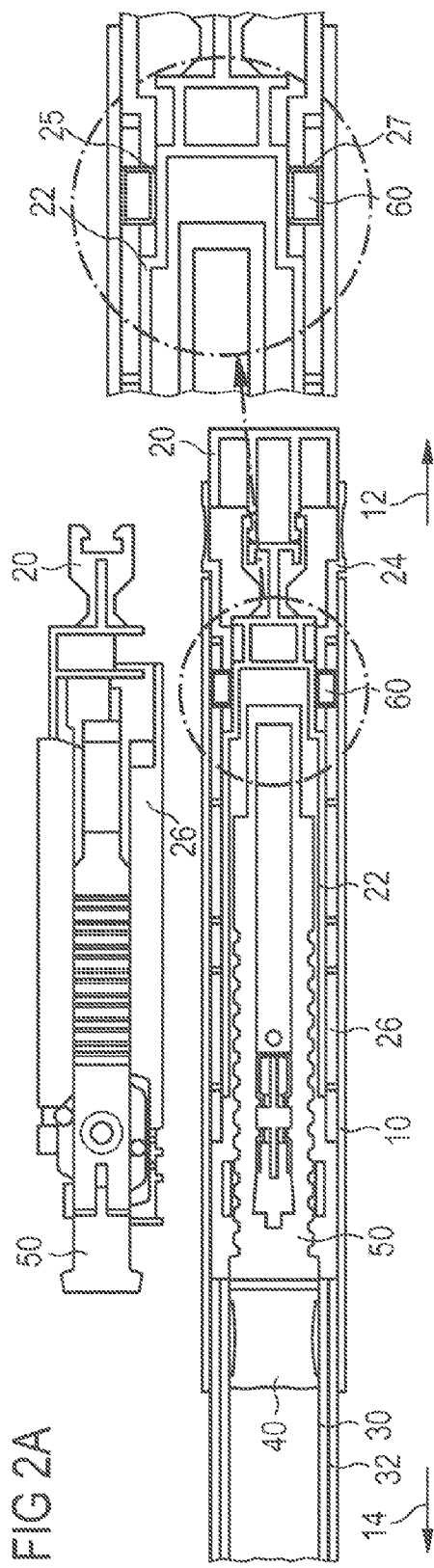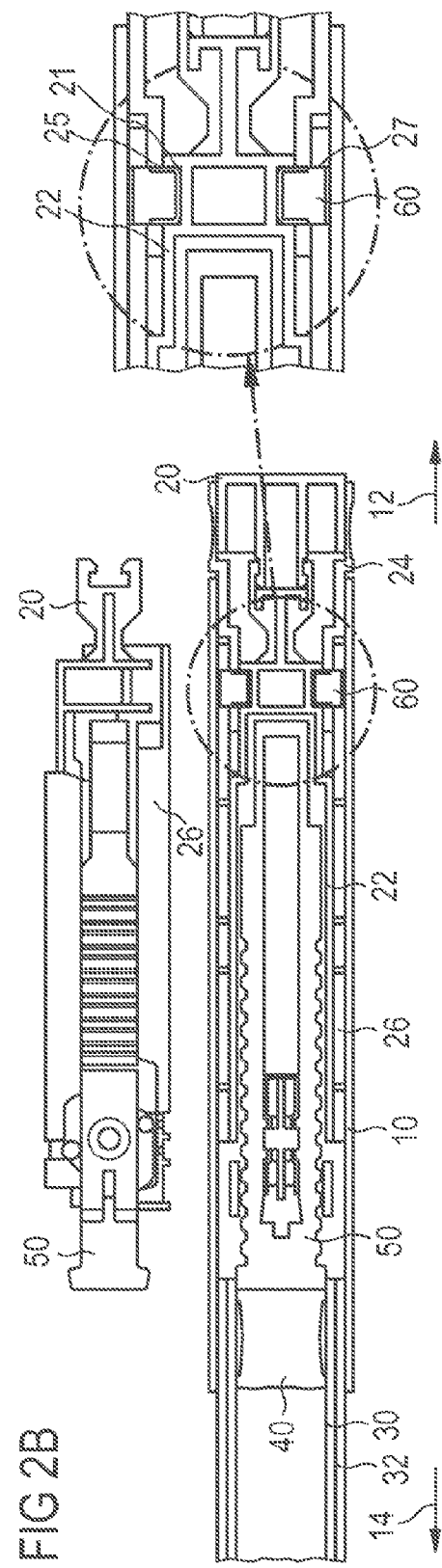

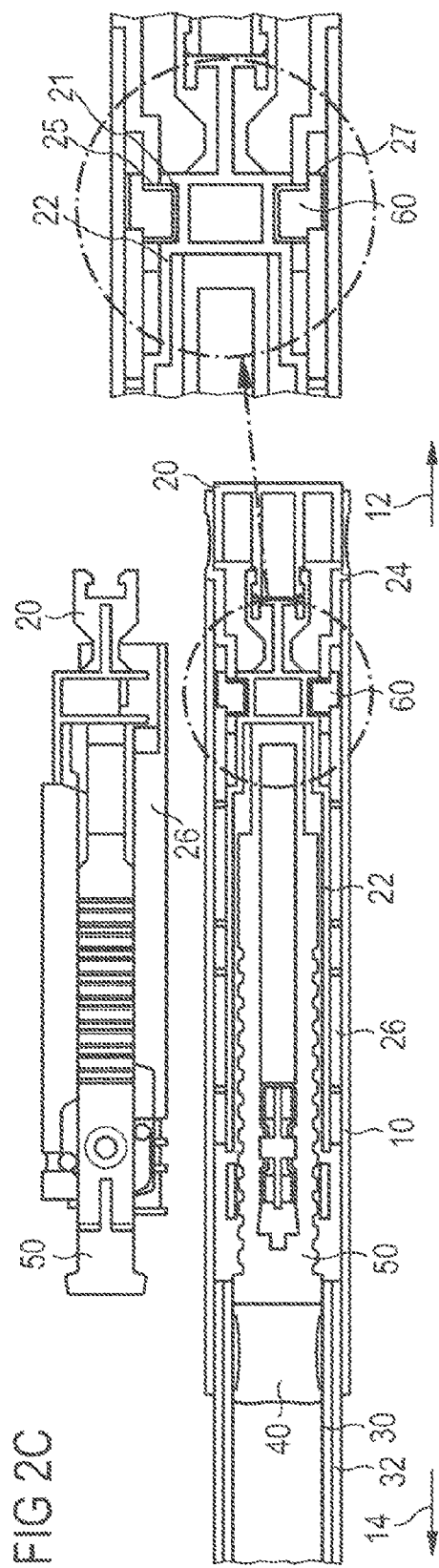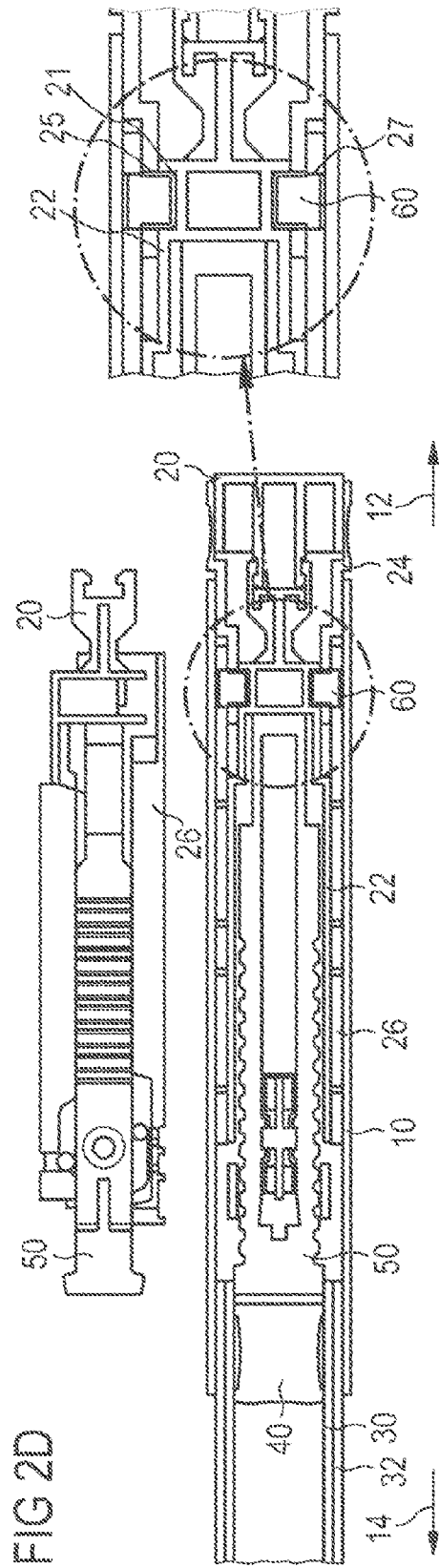

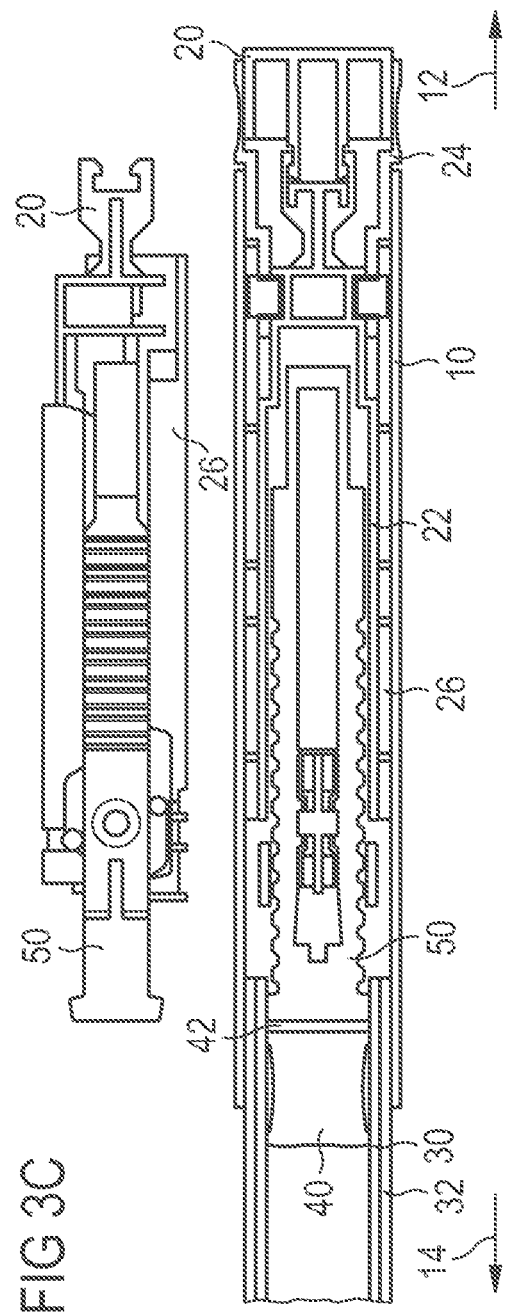

ASSEMBLY FOR USE IN A DRUG DELIVERY DEVICE

CROSS REFERENCE TO RELATED APPLICATIONS

The present application is a U.S. National Phase Application pursuant to 35 U.S.C. §371 of International Application No. PCT/EP2010/064409 filed Sep. 29, 2010, which claims priority to European Patent Application No. 09171750.4 filed on Sep. 30, 2009. The entire disclosure contents of these applications are herewith incorporated by reference into the present application.

FIELD OF INVENTION

The present invention relates to an assembly for use in a drug delivery device.

BACKGROUND

Drug delivery devices are generally known for the administration of a medicinal product, for example insulin or heparin, but also for other medicinal products for self-administration by a patient. Most of the drug delivery devices are pen-type injectors, which dispense a pre-set dose of a fluid medicinal product.

Before the first use of a drug delivery device the user usually has to prime the drug delivery device. Users who are unfamiliar with such pen-type injectors may fail or incorrectly prime their drug delivery device before dispensing the first dose.

SUMMARY

It is an object of the present disclosure to provide an assembly for use in a drug delivery device, which helps to improve user friendliness and helps to improve the accuracy of the first dispensed dose of a fluid medicinal product.

According to a first aspect of the present disclosure, an assembly for use in a drug delivery device is provided, comprising a proximal end, a distal end and a moveable member, a dose member, a fixed member and coupling means. In a first state of the assembly, the moveable member is moveable in an axial direction with respect to the fixed member and with respect to the dose member. In this state, the coupling means retains the dose member to the fixed member. In a second state of the assembly, the moveable member is in permanent connection with the dose member by means of the coupling means and the dose member is released from the fixed member. In this state, the assembly is configured to set and dispense a dose of a fluid medicinal product out of an assembled cartridge by movement of the dose member.

The assembly comprises a distal end, where the medicinal product may be dispensed out of an assembled medicament cartridge and a proximal end, which is opposite to the distal end.

Preferably, the fixed member may be rigidly mounted to a body of the drug delivery device. In the first state of the assembly, the dose member is coupled with the fixed member by the coupling means. In this position, the coupling means rigidly retains the dose member to the fixed member, such that the dose member cannot move relative to the body in any direction. This prevents the user from accidentally dispensing a dose of a fluid medicinal product without previously priming the drug delivery device.

However, in the first state, the moveable member is moveable with respect to the dose member and also with respect to the fixed member. By moving the moveable member, the assembly can be transferred to the second state.

In the second state of the assembly, the moveable member is coupled with the dose member, whereby the dose member is released from the fixed member. Due to the coupling between the dose member and the moveable member, the dose member is now axially displaceable with respect to the fixed member.

In the second state, it is possible for the user to set and dispense doses of a fluid medicinal product out of an assembled medicament cartridge. The user may pull the dose member axially in proximal direction to set a dose of a fluid medicinal product and then the user may push the dose member back in distal direction to dispense a dose.

By pushing the dose member in the distal direction the dose member drives the drive mechanism, thereby advancing a piston rod in distal direction. This results in a bung traversing in distal direction in an assembled medicament cartridge to expel the medicinal product from the cartridge.

The assembly described herein may be used for fixed dose pens as well as for variable dose pens.

A housing may be provided which comprises a body and a cartridge holder. The fixed member may be permanently rigidly mounted to the body and thereby to the housing.

In a preferred embodiment, the fixed member is permanently attached to a housing.

In another preferred embodiment, the fixed member and the housing are integrally formed.

The fixed member and the body, which is part of the housing, may comprise two separate parts that are rigidly connected to each other or, as an alternative, both parts can be integrally formed and thereby form one single component.

According to another preferred embodiment in the first state of the assembly, the coupling means engage with the fixed member and the dose member to prevent movement of the dose member relative to the housing.

Preferably, in the first state of the assembly, a priming operation is enabled in order to remove tolerance gaps between drive mechanism components before the first use of the device.

Before the first use of the drug delivery device the user usually has to prime the drug delivery device. During a priming operation the mechanism of the device is advanced in order to take up any gaps between the drive mechanism components as well as between the piston rod and the bung. Furthermore, air can be expelled that may be in the needle, thereby ensuring a safe and accurate first dose.

Due to the coupling between the fixed member and the dose member, it is not possible for the user to set a dose of a fluid medicinal product while the assembly is in the first state. Thereby, the risk of accidentally injecting prime fluid is reduced. Also, the accuracy of the first dispensed dose is increased.

In the first state, the user is allowed to prime the drug delivery device. To prime the drug delivery device, the moveable member is moved in distal direction. Thereby, the dose member is decoupled from the fixed member and coupled to the moveable member by a coupling means.

In a preferred embodiment, the moveable member is at least partly arranged inside the dose member.

The dose member may have a cylindrical recess through which the moveable member can be moved. The moveable member may be part of the drive mechanism to advance a piston rod inside an assembled medicament cartridge.

In another preferred embodiment in the first state of the assembly, a proximal part of the moveable member is moved in distal direction through the dose member.

In the first state of the assembly, the user may push the proximal part of the moveable member. Thereby, the moveable member is moving in the distal direction through a for example cylindrical recess in the dose member.

In a preferred embodiment in the first state of the assembly, a volume of a fluid medicinal product is dispensed out of an assembled medicament cartridge while the moveable member is moved in the distal direction.

To prime the device, the user pushes the moveable member in distal direction. The moveable member then drives the drive mechanism of the drug delivery device in the same way as for dispensing a dose of a fluid medicinal product. As a result of this, the tolerance gaps between drive mechanism components may be all taken up correctly to ensure that the first dose is accurate.

Due to the applied pressure onto the bung, a bung in an assembled medicament cartridge is moved in the distal direction. Thereby, a small amount of fluid medicinal product is dispensed out of the medicament cartridge.

In another preferred embodiment in the second state of the assembly, the moveable member and the dose member are suitable for advancing a piston rod and thereby driving the bung of an assembled cartridge to dispense doses of a fluid medicinal product.

In the second state of the assembly, a dose of a fluid medicinal product can be set and dispensed. The moveable member and the dose member are coupled to each other. The user may pull the dose member in the proximal direction and thereby set a dose of the fluid medicinal product. To dispense the set dose of the fluid medicinal product, the user pushes the dose member in the distal direction. Thereby, a bung is advanced in an assembled medicament cartridge and medicinal product is dispensed.

When a dose is dispensed by pushing the dose member in the distal direction, the moveable member may also be pushed in distal direction.

In an embodiment, the drive mechanism comprises a piston rod. This piston rod is advanced in the distal direction by pushing the moveable member in distal direction.

Thus, due to the movement of the piston rod, a bung of an assembled cartridge is moved.

In any case, the delivered amount of medicinal product can be fixed or variable. In the second state of the assembly, the user is enabled to dispense an exact volume of the fluid medicinal product.

In a preferred embodiment, the assembly comprises a safety feature to releasably retain the assembly in the first state.

The moveable member may protrude from the dose member while the assembly is in the first state. The safety feature holds this position between the moveable member and the dose member. The safety feature may comprise a detent feature and helps to prevent rattling of the mechanism before use. Additionally, the safety feature prevents accidental priming.

When the moveable member is pushed in distal direction, it may thereby be pushed over the detent feature. This action enables the user to prime the drug delivery device and to expel a quantity of priming fluid out of an assembled medicament cartridge.

According to another preferred embodiment in the first state, the moveable member interacts with the coupling means when being moved in distal direction.

The coupling means may be U-shaped lock-clip or a flexible arm. The moveable member may comprise an associated recess. When the user pushes the moveable member through the dose member, the recess of the moveable member aligns with the, for example U-shaped, coupling means.

The coupling means may be outwardly flexed by an outer surface of the movable member, imparting an inwardly directed radial load onto the moveable member. When the moveable member moves in distal direction so that the recess is aligned with the coupling means, the coupling means deflects into the recess of the moveable member as a result of the inwardly directed radial load. This interaction between the moveable member and the coupling means may decouple the dose member from the fixed member and may couple the dose member to the moveable member.

In a particularly preferred embodiment, the interaction of the moveable member with the coupling means results in a coupling of the dose member and the moveable member and thus helps to establish the second state.

In another preferred embodiment, the interaction of the moveable member with the coupling means results in a decoupling between the dose member and the fixed member and thus helps to establish the second state.

In the first state of the assembly, the fixed member and the dose member are coupled by the coupling means. Due to the interaction of the moveable member and the coupling means, the coupling means together with the dose member release their engagement with the fixed member and couple with the moveable member.

According to another preferred embodiment, the dose member is located at the proximal end of the assembly.

The location of the dose member should allow the user to operate the drug delivery device safely and conveniently. Thus, the position of the dose member is of importance.

If the needle unit is located at the distal end of the drug delivery device, the safest location to operate the device without the risk of inadvertently touching the needle and thereby getting hurt is the proximal end of the drug delivery device.

In a preferred embodiment, the coupling means is biased, such that it releases from engagement with the fixed member to engage the moving member while the assembly is being transferred from the first state to the second state.

The decoupling of the dose member from the fixed member and the coupling of the dose member with the moveable member can be achieved in various ways. One is by applying a force onto the coupling means to release the coupling means from the fixed member.

Another way is an arrangement where the coupling means is biased, such that it releases from the fixed member as soon as this is possible.

In another preferred embodiment, the coupling means comprises at least two different elements. The coupling means may comprise two ore even more elements.

In a preferred embodiment, the at least one element of the coupling means is an integrally formed part of the fixed member. The coupling means can thus be formed such that it might be part of the fixed member. For example, the coupling means may comprise a flexible arm, which is located on the fixed member.

According to another preferred embodiment, the moveable member comprises at least two different components.

One component forms the proximal part of the moveable member and another component forms the distal part of the moveable member and is located inside the body of the drug delivery device. Clip features may constrain these two components together.

The connection between the two parts of the moveable member could be a rigid connection or the clip feature could connect both parts. The clip feature may prevent relative axial movement between the two parts, but allows relative rotational movement. This means if the user misuses the pen when it is in the first state, and tries to turn the distal part of the moveable member, it will not impart excessive torque onto the drive mechanism. This prevents the user from damaging the drive mechanism or priming the drug delivery device accidentally by a rotational movement of the distal part of the moveable member.

According to another preferred embodiment, a back-off means is located between the movable member and the fixed member to remove the pressure from the bung when the user removes pressure from the moveable member.

This back-off means can comprise for example a spring. This spring may be compressed during the distal movement of the movable member in which the piston rod is driven. The piston rod thereby applies a pressure onto a cartridge bung. If the user removes the pressure from the moveable member, the pressure from the bung is also removed because of elastic behaviour of the spring moves the moveable member slightly in the proximal direction, which releases the pressure on the piston rod.

According to another aspect of the present disclosure, a method for setting up a drug delivery device is provided, the device comprising a moveable member, a dose member, a fixed member and coupling means, the method comprising: pushing the moveable member in the distal direction thereby causing a coupling of the dose member with the moveable member by means of the coupling means and causing a decoupling of the dose member and the fixed member.

This method for setting up a drug delivery device helps to minimize the risk of users forgetting to undertake the prime set-up step by providing a visual indication to disencourage the user from injecting the prime fluid and encourage the user to prime the pen-type injector correctly before use.

According to a preferred embodiment indication markings may be applied to an external surface of the moveable member to indicate that priming should be made. These markings may become hidden from view when the moveable member is pushed inside the dose member i.e. when priming is completed.

The advantage of this method and assembly is that the assembly and therefore the drug delivery device has a prime set-up step which is different from the set-and-dispense step. This different step draws the user's attention to the requirement to prime, rather than relying on accompanying instructions.

The term "medicinal product", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-($\omega$-carboxyheptadecanoyl)-des(B30) human insulin and B29-N-($\omega$-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

In the following, the invention is described in further detail with reference to the drawings, wherein
FIG. 2a shows a drug delivery device in a pre-primed state;
FIG. 2b shows the drug delivery device during the priming process;
FIG. 2c shows the drug delivery device at the end of the priming process;
FIG. 2d shows the drug delivery device after back-off has occurred at the end of the priming mechanism;
FIG. 3c shows the backed-off condition after delivery of the first dose from the drug delivery device.

DETAILED DESCRIPTION

Some preferred embodiments of the assembly according to the present disclosure will now be discussed with reference to FIG. 1, FIG. 2a, 2b, 2c, 2d, FIG. 3a, 3b, 3c and FIG. 4. Identical reference signs denote identical or comparable components.

Figure 1:
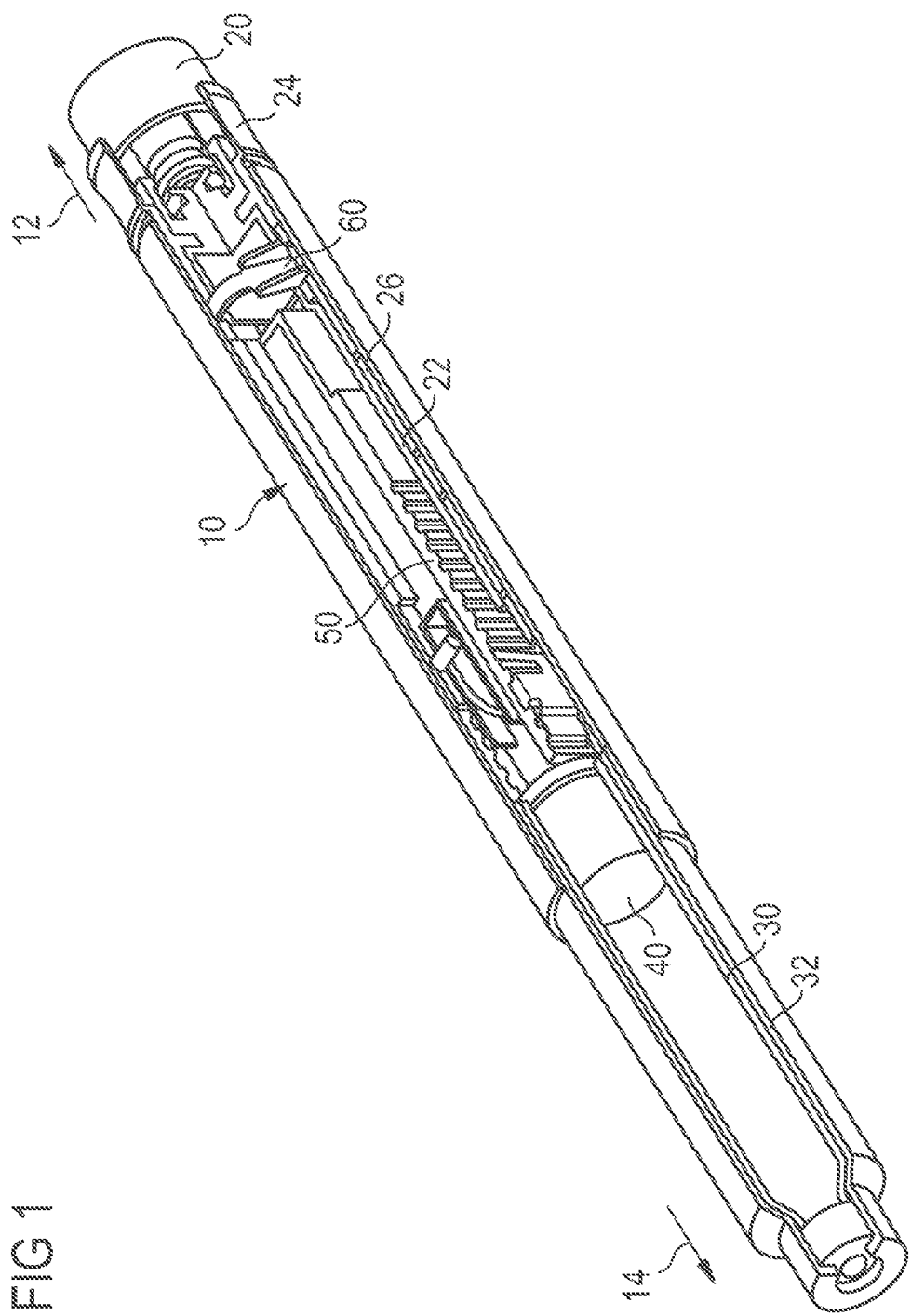
FIG. 1 shows a cut away view of a drug delivery device comprising an assembly according to a first embodiment of the present disclosure.

FIG. 1 shows a cutaway view of the drug delivery device according to one embodiment of the present disclosure. The housing of the drug delivery device comprises two parts, a body 10 and a cartridge holder 32. Within the cartridge holder 32, a medicament cartridge 30 is located, which contains a number of doses of a fluid medicinal product.

The medicinal product may be injected by means of a needle, that is not explicitly shown, and which can be attached to the distal end of the drug delivery device.

During use, the cartridge holder 32 is permanently attached to the body 10 of the pen-type injector. The assembly comprising inter alia the fixed member, the moveable member, the dose member and the coupling means is located substantially within the body 10 of the drug delivery device.

The fixed member 26 is permanently rigidly mounted to the body 10. The coupling means 60 is a spring steel component and is essentially U-shaped. When the pen-type injector is delivered to the customer it is in its pre-primed state, in which recesses in the fixed member 26 and the dose member 24 capture the coupling means 60. This arrangement is shown in FIG. 2a.

The coupling means 60 is outwardly flexed by an outer surface of the distal part 22 of the moveable member 20, thus imparting an inward radially directed load onto the distal part 22 of the moveable member 20. In this position, the coupling means 60 rigidly retains the dose member 24 in its axial position relative to the fixed member 26, such that the dose member 24 cannot move relative to the body 10 in an axial direction.

The dose member 24 has a cylindrical recess in its proximal end into which the moveable member 20 can fit. The moveable member 20 protrudes from the dose member 24 and is lightly held in position by a safety feature, which is not explicitly shown and which is located between the dose member 24 and the moveable member 20. The safety feature prevents rattling of the mechanism before use and helps to prevent accidental priming.

To prime the device, the user pushes the moveable member 20 in distal direction 14. The moveable member 20 then drives the drive mechanism of the drug delivery device in the same way as for dispensing a dose of a fluid medicinal product.

Thereby, a bung 40 in an assembled medicament cartridge 30 is moved in distal direction 14 by means of a piston rod 50. During the priming process, any gaps are taken up between the drive mechanism components and also between the piston rod 50 and the bung 40 and a small amount of fluid medicinal product is dispensed out of the medicament cartridge 32.

In the second state of the assembly, a dose of a fluid medicinal product can be set and dispensed. The moveable member 20 and the dose member 24 are coupled with each other. The user may pull the dose member 24 in proximal direction 12 and thereby set a dose of the fluid medicinal product. To dispense the set dose of the fluid medicinal product, the user pushes the dose member 24 in distal direction 14. Thereby, a bung 40 is advanced by means of a piston rod 50 in an assembled medicament cartridge 32 and medicinal product is dispensed.

By pushing the dose member 24 in distal direction 14, the moveable member 20 may be pushed in distal direction 14 and vice versa.

FIGS. 2a to 2d show the priming of the drug delivery device.

In FIG. 2a, the pre-prime state of the drug delivery device is shown in a cutaway view. The coupling means 60 is a spring steel component and is essentially U-shaped. In the pre-prime state, recesses 25, 27 in the fixed member 26 and the dose member 24 capture the coupling means 60.

In FIG. 2b, the assembly is shown in a partially-primed state in a cutaway view. To prime the device, the user pushes the moveable member 20 axially in the distal direction 14, into the dose member 24. This action drives the distal end 22 of the moveable member 20 forwards. The distal end 22 of the moveable member 20 drives the mechanism in the same way as for dispensing a dose of a fluid medicinal product, resulting in the cartridge bung 40 traversing in the distal direction 14 to expel the prime fluid.

The distal part 22 of the moveable member 20 comprises a recess 21 such that when the moveable member 20 is fully pushed into the dose member 24, the recess 21 of the moveable member 20 aligns with the coupling means 60.

The coupling means 60 then deflects into the recess 21 in the distal part 22 of the moveable member 20, resulting in a rigid connection between the dose member 24 and the distal end 22 of the moveable member 20 and at the same time releasing the dose member 24 from the fixed member 26.

This will create an audible snap that will give the user feedback that the moveable member 20 has been pushed in sufficiently far.

As shown in FIG. 2c, with pressure from the user still applied to the moveable member 20, the dose member 24, the moveable member 20 and the distal part 22 of the moveable member 22 now move in the distal direction 14 together to complete the dispense of priming fluid. This compresses a back-off spring, which is not explicitly shown, between the distal end 22 of the movable member 20 and the fixed member 26.

In FIG. 2d the post priming backed-off condition is shown. The assembly comprises back-off means to remove the pressure from the bung 40 when the user removes pressure from the moveable member 20. This action transfers the assembly from the state shown in FIG. 2c to that shown in FIG. 2d. The assembly and therefore the drug delivery device is then ready to set and dispense doses of medicinal product.

Figure 3A:
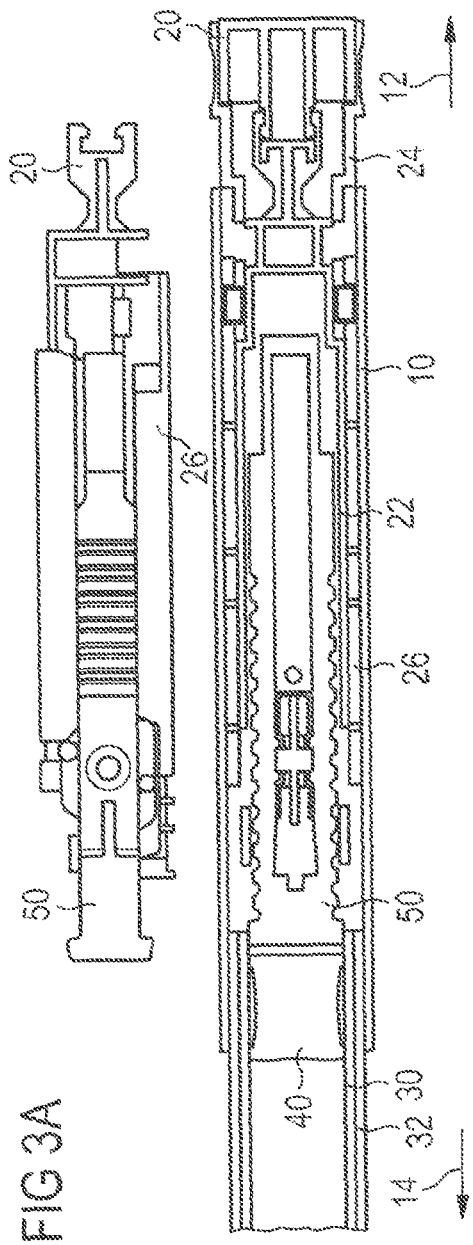
FIG. 3a shows a drug delivery device during the setting of the first dose.

FIG. 3a shows a primed drug delivery device, which is ready to set and dispense a dose of a fluid medicinal product.

After priming the drug delivery device, which is shown in FIGS. 2a to 2d, the user pulls the dose member 24 axially in the proximal direction 12 relative to the body 10 to set a dose of a fluid medicinal product, which is contained in an assembled medicament cartridge 30.

After having set a dose of a fluid medicinal product, the user pushes the moveable member 20 together with the dose member 24 in distal direction 14 to dispense a dose of the fluid medicinal product.

Figure 3B:
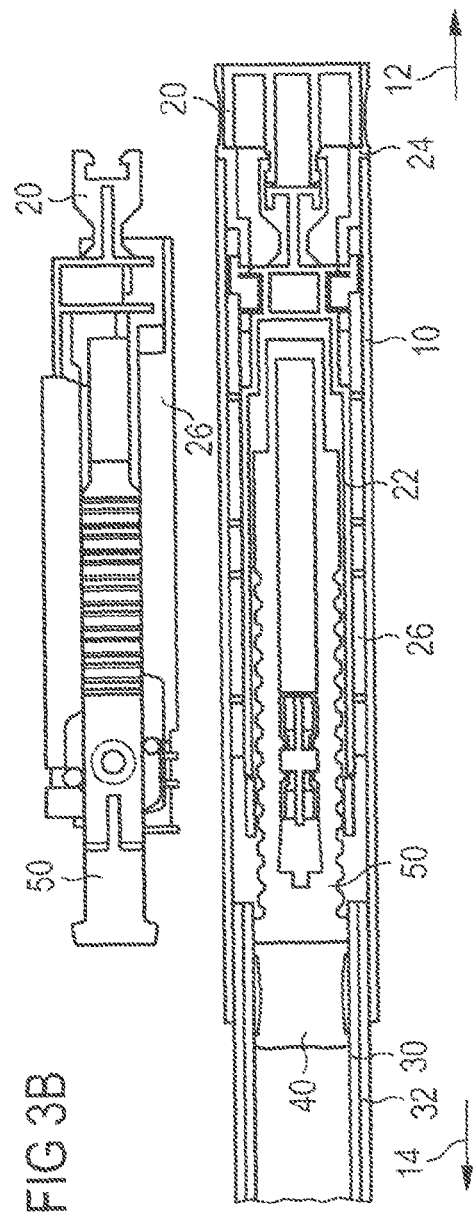
FIG. 3b shows the dispensing of the first dose.

FIG. 3b shows the drug delivery device after having dispensed the first dose of the drug delivery device.

To dispense a dose of a fluid medicinal product, the user pushes the dose member 24 in distal direction 14. Thereby, the piston rod 50 is advanced in distal direction 14. Due to the distal movement of the piston rod 50, the bung 40 is advanced in an assembled medicament cartridge 30. This movement of the bung dispenses a fluid medicinal product out of a needle, which is attached to the cartridge holder 32 and which is not explicitly shown in FIG. 3b.

FIG. 3c shows the backed-off condition after the first dose of a fluid medicinal product has been dispensed from the drug delivery device. The small gap 42 between the bung 40 and the piston rod 50 indicates that the back-off step has been performed.

Figure 4:
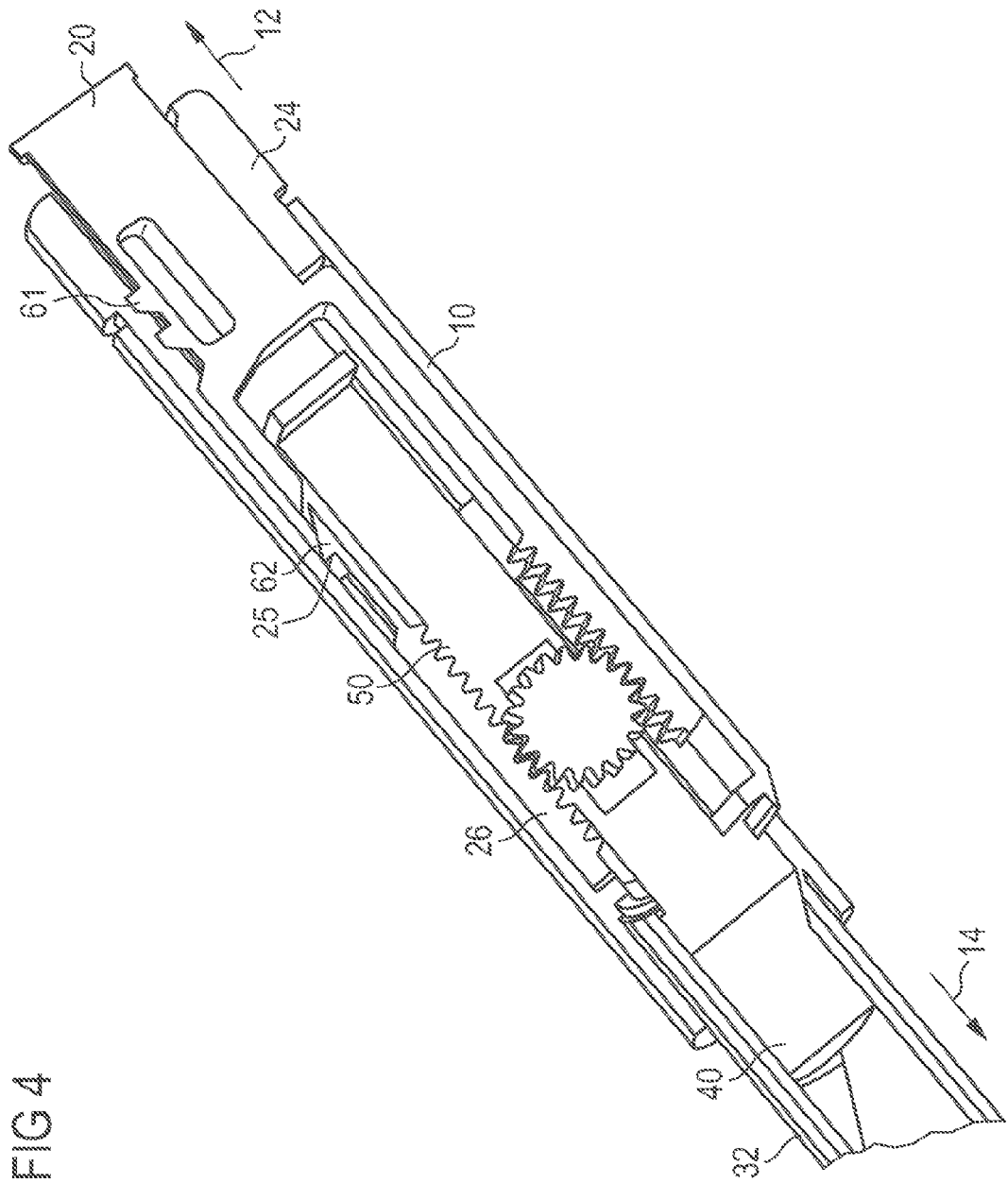
FIG. 4 shows a cutaway view of a pen-type injector according to a second embodiment.

FIG. 4 shows a cutaway view of a drug delivery device according to another embodiment of the present disclosure. In this embodiment the prime mechanism is applied to a ratchet-type piston rod 50. The moveable member 20 is one component, which may be manufactured for example out of plastic. Two additional features 61, 62 are moulded into the plastic components.

The safety feature is clip feature 61 that retains the moveable member 20 in its pre-prime position relative to the dose member 24 until the user wishes to prime the device. The clip features 61 allow the moveable member 20 to be pushed into the dose member 24 and provide a snap to permanently rigidly fix the moveable member 20 to the dose member 24 on completion of priming.

A flexible arm 62 on the fixed member 26 is not deflected in the pre-prime state and clips over a recess 25 in the dose member 24 to prevent the user from pulling the dose member 24 in the proximal direction 12 relative to the body 10.

On completion of priming, a feature on the movable member 20 abuts the flexible arm 62 and deflects it out of engagement with the dose member 24 so that the user can now pull the dose member 24 in the proximal direction 12 to set a dose of a fluid medicinal product.

The present examples and embodiments are to be considered as illustrative and not restrictive, and the invention is not to be limited to the details given herein, but may be modified within the scope and equivalence of the appended claims.

The invention claimed is:

1. An assembly for a drug delivery device comprising a proximal end, a distal end, a moveable member, a dose member, a fixed member and a coupling means,
   wherein in a first state, (i) the moveable member is moveable in an axial direction with respect to the fixed member and the dose member and (ii) the coupling means retains the dose member to the fixed member by interacting with both the dose member and the fixed member to form a connection between the dose member and the fixed member, and
   wherein in a second state of the assembly, (i) the coupling means (a) permanently connects the moveable member with the dose member and (b) releases the connection between the dose member and the fixed member formed by the coupling means and (ii) the assembly is configured to set and dispense a dose of a fluid medicinal product out of an assembled cartridge by movement of the dose member.

2. The assembly of claim 1, wherein the fixed member is permanently attached to a housing.

3. The assembly of claim 2, wherein the fixed member and the housing are integrally formed.

4. The assembly of claim 1, wherein in the first state, the coupling means engage with the fixed member and the dose member to prevent movement of the dose member relative to the housing.

5. The assembly of claim 1, wherein the moveable member is at least partly arranged inside the dose member.

6. The assembly of claim 5, wherein in the first state of the assembly, a proximal part of the moveable member is moved in distal direction through the dose member.

7. The assembly of claim 6, wherein in the first state of the assembly a volume of a fluid medicinal product is dispensed out of an assembled medicament cartridge when the moveable member is moved in distal direction.

8. The assembly of claim 1, wherein in the second state of the assembly the moveable member and the dose member are suitable for advancing a piston rod and thereby driving a bung of an assembled cartridge to dispense doses of a fluid medicinal product.

9. The assembly of claim 1, wherein the assembly comprises a clip feature to releasably retain the assembly in the first state.

10. The assembly of claim 1, wherein in the first state, the moveable member interacts with the coupling means when being moved in a distal direction.

11. The assembly of claim 10, wherein the interaction of the moveable member with the coupling means results in a coupling of the dose member and the moveable member.

12. The assembly of claim 10, wherein the interaction of the moveable member with the coupling means results in a decoupling between the dose member and the fixed member.

13. The assembly of claim 1, wherein the dose member is located at the proximal end of the assembly.

14. The assembly of claim 1, wherein the coupling means is biased, such that it releases from engagement with the fixed member to engage the moving member while the assembly is being transferred from the first state to the second state.

15. The assembly of claim 1, wherein the coupling means comprises at least two different elements.

16. The assembly of claim 15, wherein at least one element of the coupling means is an integrally formed part of the fixed member.

17. The assembly of claim 1, wherein the moveable member comprises at least two different components.

18. The assembly of claim 1, wherein a back-off means is located between the movable member and the fixed member to remove the pressure from the bung when the user removes pressure from the moveable member.

19. The assembly of claim 1, wherein when the assembly is in the first state, priming of the drug delivery device is allowed where the moveable member is moved in a distal direction to remove tolerance gaps between drive mechanism components.

20. The assembly of claim 1, wherein the fixed member comprises a first recess,
   wherein the dose member comprises a second recess, and
   wherein, in the first state, the coupling means forms the connection between the dose member and the fixed member when the first recess and the second recess capture the coupling means.

21. The assembly of claim 1, wherein the moveable member comprises a recess, and
   wherein after the movable member is moved axially relative to the dose member, the recess aligns with the coupling means and the coupling means then deflects into the recess, wherein deflecting into the recess results in (i) permanently connecting the dose member and the moveable member and (ii) releasing the connection between the dose member and the fixed member.

22. The assembly of claim 1, wherein after the assembly changes from the first state to the second state, the moveable member remains permanently connected with the dose member.

23. The assembly of claim 1, wherein the coupling means is a spring.

* * * * *